United States Patent [19]

Das et al.

[11] Patent Number: 4,912,124

[45] Date of Patent: Mar. 27, 1990

[54] ANTIFUNGAL DERMATOLOGICAL SOLUTION

[75] Inventors: Sudeb Das, Dayton; Darius D. Dubash, Somerville, both of N.J.

[73] Assignee: Ortho Pharmaceutical Corporation, Raritan, N.J.

[21] Appl. No.: 583,081

[22] Filed: Feb. 23, 1984

[51] Int. Cl.$^4$ ............................................ A61K 31/415
[52] U.S. Cl. ..................................................... 514/399
[58] Field of Search ........................ 424/269; 514/399

[56] References Cited

U.S. PATENT DOCUMENTS 3,717,655  2/1973  Godefroi et al. .
3,989,815  11/1976  Rajadhyaksha ..................... 424/274

OTHER PUBLICATIONS

U.S. Pharmacopeia XX, Supplement 3, pp. 193–195.
Physical and Technical Pharmacy, edited by Burlage, Lee and Rising, McGraw-Hill, pp. 430–433.
Physical Pharmacy, Martin, Swarbrick and Cammarata, pp. 462–465.

Primary Examiner—Joseph A. Lipovsky
Attorney, Agent, or Firm—Lawrence D. Schuler; Steven P. Berman

[57] ABSTRACT

Alcohol/aqueous solutions of certain relatively insoluble imidazole derivatives, particularly micronazole and miconazole nitrate, are prepared to concentrations of at least 1.0 percent by weight active agent. The solutions are pharmacologically acceptable for topical application as the treatment of fungal skin infections and are readily applied by means of a pump sprayer.

7 Claims, No Drawings

ANTIFUNGAL DERMATOLOGICAL SOLUTION

FIELD OF INVENTION

This invention relates to antifungal solutions for dermatological use and more particularly to solvent solutions of certain imidazole derivatives which are effective in treating fungal skin infections.

BACKGROUND

Imidazole derivatives of the class 1-($\beta$-aryl)ethylimidazole ethers useful for their antifungal properties are disclosed in U.S. Pat. No. 3,717,655, incorporated herein by reference for its teaching of the preparation and use of such compounds. As described in this patent, imidazole derivatives of the defined class have the formula:

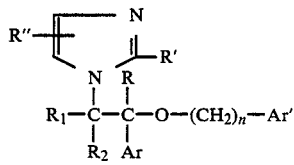

and the therapeutically active acid addition salts thereof, wherein:

R, $R_1$ and $R_2$ are each a member selected from the group consisting of hydrogen and lower alkyl; n is the integer 1 or 2;

Ar is a member selected from the group consisting of phenyl, mono-, di- and tri-halophenyl, lower alkylphenyl, lower alkoxyphenyl, thienyl and halothienyl;

Ar' is a member selected from the group consisting of phenyl, mono-, di- and tri-halophenyl, mono- and di-(lower alkyl) phenyl, lower alkoxyphenyl and cyanophenyl;

R' is a member selected from the group consisting of hydrogen, methyl and ethyl; and R'' is a member selected from the group consisting of hydrogen and methyl.

The '655 patent further discloses that compositions comprising such imidazole derivatives as the active ingredient in a solvent or a solid, semi-solid or liquid diluent or carrier provide an effective method of combatting fungus growth. According to the patent, "The subject compounds can be used in suitable solvents or diluents, in the form of emulsions, suspensions, dispersions or ointment, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives."

"Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents with a flash point of at least 30° C., such as, for example, isopropanol dimethylsulfoxide, hydrogenated naphthalenes and alkylated napthalenes. It is, of course, also possible to use mixtures of solvents. Solutions can be prepared in the usual way, if necessary, with assistance of solution promoters. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent."

"When the subject compounds are employed in combination with suitable carriers, e.g., in solution, suspension, duct, powder, ointment, emulsion, and the like forms, a high activity over a very high range of dilution is observed. For example, concentrations of the active ingredient ranging from 0.1–10 percent by weight, based on the weight of composition employed, have been found effective in combatting fungi or bacteria. Of course, higher concentrations may also be employed as warranted by the particular situation."

An example of an imidazole solution is given in Example LX of the '655 patent where five parts of 1-[p-chloro-$\beta$-(2,6-dichlorobenzyloxy)phenethyl] imidazole are dissolved in 95 parts of alkylated naphthalene and used as a spray for the treatment of fungus infected subjects or on walls, floors or other objects to prevent infection by fungi. Such solutions of the imidazole derivatives, while effective antifungal compositions, are obviously not suitable for dermatological use due to the presence of the strong organic solvent which has an irritating and defatting effect on tissue.

A preferred imidazole derivative for use in the present invention is 1-[2,4-dichloro-$\beta$-(2,4-dichlorobenzyloxy)phenethyl] imidazole nitrate which has the common name miconazole nitrate. The solubility of miconazole nitrate in water is 0.03% and in ethanol 0.76% weight/volume. The solubility is thus too low in such solvents to provide the desired concentration of at least one percent pharmaceutical active agent in solution for use as a dermatological product.

It is accordingly an object of the present invention to provide a new solvent system for compounds of the class 1-($\beta$-aryl)ethyl-imidazole ethers. It is a further object to provide a new solvent system in which such imidazole ethers are soluble to the extent of at least one percent. It is a yet further object of this invention to provide a dermatological antifungal solution comprising at least one percent of a 1-($\beta$-aryl)ethyl-imidazole ether derivative in a pharmaceutically acceptable solvent system. A still further object of this invention is to provide a dermatological antifungal solution comprising at least one percent miconazole or miconazole nitrate in a novel solvent system. These and other objects of this invention will be apparent from the ensuing description and claims.

SUMMARY

The dermatological antifungal solutions of the present invention comprise a therapeutically effective amount of at least about 1.0 percent by weight of an imidazole derivative of the type 1-($\beta$-aryl)ethyl-imidazole in a solvent system consisting essentially of:

(i) 20 to 80% by weight of a said system of a polar solvent comprising 40 to 100% of ethyl or benzyl alcohol or mixtures thereof and 0 to 60% water;

(ii) 5 to 70% by weight of said system of a solubilizing agent comprising a polyhydric alcohol or an ester or alkyl substituted derivative thereof or mixtures thereof;

(iii) 0 to 5% of a nonionic or amphoteric surfactant; and (iv) 0 to 15% of a cosmetic humectant.

In a preferred formulation, the imidazole derivative is miconazole or miconazole nitrate. Solutions containing at least about 1.0 percent by weight of miconazole/miconazole nitrate, and preferably from about 1.5 to 2.5 percent by weight, are effective antifungal compositions useful in treating skin infections, are pharmacologically acceptable for topical use and dry rapidly for the convenience of the user.

DESCRIPTION OF PREFERRED EMBODIMENTS

The 1-($\beta$-aryl)imidazole ethers utilized as the active antifungal agent in the compositions of the present invention are known compounds, the preparation of which is disclosed in U.S. Pat. No. 3,717,655. Such compounds have the formula:

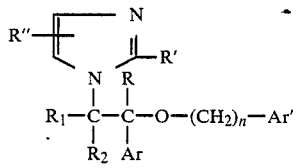

wherein R, $R_1$ and $R_2$ are each a member selected from the group consisting of hydrogen and lower alkyl;

n is the integer 1 or 2;

Ar is a member selected from the group consisting of phenyl, mono-, di- and tri-halophenyl, lower alkylphenyl, lower alkoxyphenyl, thienyl and halothienyl;

Ar' is a member selected from the group consisting of phenyl, mono-, di- and tri-halophenyl, mono- and di(-lower alkyl) phenyl, lower alkoxyphenyl and cyanophenyl;

R' is a member selected from the group consisting of hydrogen, methyl and ethyl; and R" is a member selected from the group consisting of hydrogen and methyl.

As used herein, "lower alkyl" and "lower alkoxyl" may be straight or branch chained saturated hydrocarbons having from 1 to about 6 carbons, such as, for example, methyl, ethyl, propyl, isopropyl, butyl, pentyl, hexyl and the like alkyls, and, respectively, the corresponding alkoxys such as methoxy, ethoxy, propoxy, isopropoxy, etc. The preferred lower alkyl and lower alkoxy are methyl and methoxy, respectively. The term "halo" refers to halogens of atomic weight less than 127, i.e., fluoro, iodo, bromo, and chloro.

A particularly preferred imidazole ether representative of the above compounds is miconazole, 1-[-2,4-dichloro-$\beta$-(2,4-dichlorobenzyloxy)phenethyl] imidazole as the base or as the nitrate salt having the formula:

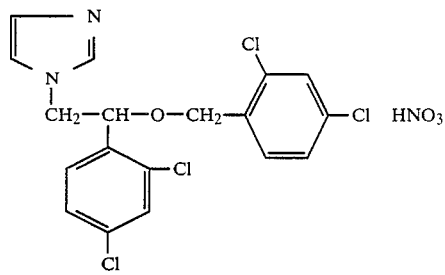

The imidazole ethers in general and the miconazoles in particular have very low solubilities in most solvents suitable for use in topical pharmaceutical compositions such as in the threatment of fungal skin infections. The solubility of miconazole nitrate, for example, in several common solvents has been determined to be as follows:

| Solvent | G/100 ml. |
| --- | --- |
| Water | 0.03 |
| NaOH | Insoluble |
| HCl 0.1 N | 0.05 |
| 40% PG/water | 0.13 |
| Propylene Glycol | 0.15 |
| PEG 300 | 0.13 |
| Methanol | 1.5 |
| Ethanol | 0.76 |
| 2-Propanol | 0.13 |
| Acetone | 0.34 |
| Hexane | 0.03 |
| Chloroform | 0.31 |
| Ethyl Acetate | 0.07 |
| Benzene | 0.05 |
| Methyl Isobutylketone | 0.04 |
| Tetrahydrofuran | 0.2 |

In the treatment of fungal skin infections, it is desirable that the antifungal agent be easily applied with a minimum of discomfort and inconvenience to the user. Miconazole nitrate has already found wide application as an over-the-counter antifungal preparation in the form of ointment, creams and dry powders. Attempts to formulate miconazole nitrate as a non-aerosol solution which could be dispensed via a pump sprayer were frustrated by the extremely low solubility of miconazole nitrate in pharmaceutically acceptable solvents. The present invention overcomes this problem by providing an acceptable solvent system capable of dissolving from 1.0 to 2.5 percent or more by weight miconazole nitrate to provide an easily dispensed, quickly drying and effective antifungal composition.

The solvent system according to this invention consists essentially of:

(i) 20 to 80% by weight of said system of a polar solvent comprising 40 to 100% of ethyl or benzyl alcohol or mixtures thereof and 0 to 60% water;

(ii) 5 to 70% by weight of said system of a solubilizing agent comprising a polyhydric alcohol or an ester or alkyl substituted derivative thereof or mixtures thereof;

(iii) 0 to 5% of a nonionic or amphoteric surfactant; and (iv) 0 to 15% of a cosmetic humectant.

The polar solvent (i) is preferably ethanol or a mixture of ethanol and water. The solubilizing agent (ii) is preferably selected from the group consisting of polyethylene glycol 200 or 400, dimethyl isosorbide, Polysorbate 20 and mixtures thereof. The surfactant (iii) which may be included in amounts up to about 5% if necessary to aid in solubilizing the imidazole derivative is preferably selected from amphoterics, alkali metal salts thereof, and Polysorbate 20 and mixtures thereof. The cosmetic humectant (iv) which may also serve as a skin emullient is preferably selected from the group consisting of glycerin, propylene glycol, methyl gluceth-10, methyl gluceth-20, PPG-10 methyl glucose ether, PPG-20 methyl glucose ether, $C_{12-15}$ alcohol benzoate, polyethylene glycol 200, polyethylene glycol 400, isopropyl palmitate, isopropyl myristate and isopropyl stearate and mixtures thereof.

Specific solvent formulations may be selected from the various suitable and preferred components as identified above or their equivalents according to the particular needs and desires of the formulator. Representative examples of some formulations providing good solvating characteristics for miconazole and miconazole nitrate are as follows:

|  |  | % w/w |
|---|---|---|
| (a) | Miconazole Nitrate | 2.20 |
|  | Polyethylene Glycol 200 | 28.00 |
|  | Di-sodium Amphoteric-2 salt (35%) | 2.00 |
|  | PPG-20 Methyl Glucose Ether | 3.50 |
|  | Benzyl Alcohol | 3.00 |
|  | Ethyl Alcohol | 35.63 |
|  | Water q.s. to | 100.00 |
| (b) | Miconazole | 2.20 |
|  | Polysorbate-20 | 36.90 |
|  | Isopropyl Palmitate, Isopropyl Myristate, Isopropyl Stearate | 4.00 |
|  | Ethyl Alcohol | 35.06 |
|  | Water q.s. to | 100.00 |
| (c) | Miconazole Nitrate | 2.20 |
|  | Dimethyl Isosorbide | 37.50 |
|  | Propylene Glycol | 37.50 |
|  | Amphoteric-17 | 3.00 |
|  | Glycerin | 3.50 |
|  | Ethyl Alcohol q.s. to | 100.00 |
| (d) | Miconazole | 2.20 |
|  | Polysorbate-20 | 7.00 |
|  | C12-15 Alcohol Benzoate | 14.00 |
|  | Glycerin | 8.00 |
|  | Ethyl Alcohol | 65.36 |
|  | Water q.s. to | 100.00 |
| (e) | Miconazole | 2.20 |
|  | Polysorbate-20 | 20.00 |
|  | Methyl Gluceth-20 | 4.00 |
|  | Propylene Glycol | 2.00 |
|  | Ethyl Alcohol | 68.21 |
|  | Water q.s. to | 100.00 |
| (f) | Miconazole Nitrate | 2.20 |
|  | Polyethylene Glycol-200 | 31.00 |
|  | Amphoteric-21 | 1.50 |
|  | Methyl Gluceth-20 | 3.50 |
|  | Benzyl Alcohol | 3.00 |
|  | Ethyl Alcohol | 37.53 |
|  | Water q.s. to | 100.00 |
| (g) | Miconazole | 2.20 |
|  | Polysorbate-20 | 20.00 |
|  | Methyl Gluceth-20 | 4.00 |
|  | Ethyl Alcohol | 35.00 |
|  | Water q.s. to | 100.00 |
| (h) | Miconazole Nitrate | 2.20 |
|  | Polyethylene Glycol-400 | 40.00 |
|  | Amphoteric-6 | 2.00 |
|  | PPG-10 Methyl Glucose Ether | 4.00 |
|  | Ethyl Alcohol | 39.00 |
|  | Water q.s. to | 100.00 |
| (i) | Miconazole Nitrate | 2.20 |
|  | Polyethylene Glycol-200 | 31.00 |
|  | Disodium Amphoteric-2 salt (70%) | 2.00 |
|  | Glycerin | 3.50 |
|  | Benzyl Alcohol | 3.30 |
|  | Ethyl Alcohol | 39.24 |
|  | Water q.s. to | 100.00 |

-continued

|  |  | % w/w |
|---|---|---|
| (j) | Miconazole | 2.20 |
|  | Polyethylene Glycol 200 | 25.00 |
|  | Disodium Amphoteric-2 salt (35%) | 3.00 |
|  | PPG-20 Methyl Glucose Ether | 3.00 |
|  | Ethyl Alcohol | 63.46 |
|  | Water q.s. to | 100.00 |

Solutions of the above formulations are readily prepared by first mixing together the solvents and surfactant to obtain a uniform clear solution. The miconazole (base or nitrate) is next dissolved in the solution with vigorous agitation. The humectant/emolient is then dissolved in the solution and finally water is added with further agitation to form the final composition. Such solutions of miconazole and miconazole nitrate are effective antifungal dermatological preparations which are easily applied from a pump sprayer, dry quickly, and are pharmacologically acceptable for topical use in the treatment of fungal skin infections.

What is claimed is:

1. A dermatological antifungal solution comprising:
   (a) a solvent system consisting essentially of 20 to 80% by weight of said system of a polar solvent comprising 40 to 100% ethyl or benzyl alcohol or mixtures thereof and 0 to 60% water; 5 to 70% by weight of said system of a solubilizing agent comprising a polyhydric alcohol or an ester or alkyl substituted derivative thereof or mixtures thereof; 0 to 5% by weight of a nonionic or amphoteric surfactant; and 0 to 15% by weight of a cosmetic humectant; and
   (b) a therapeutically effective amount equal to at least 1.0% by weight of said antifungal solution of a 1-($\beta$-aryl)ethyl-imidazole derivative soluble in said solvent system having the formula:

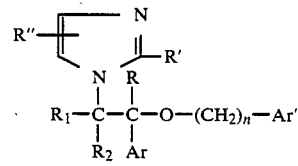

and the therapeutically active acid addition salts thereof, wherein:
   R, $R_1$ and $R_2$ are each a member selected from the group consisting of hydrogen and lower alkyl;
   n is the integer 1 or 2;
   Ar is a member selected from the group consisting of phenyl, mono-, di- and tri-halophenyl, lower alkylphenyl, lower alkoxyphenyl, thienyl and halothienyl;
   Ar' is a member selected from the group consisting of phenyl, mono-, di- and tri-halophenyl, mono- and di(lower alkyl) phenyl, lower alkoxyphenyl and cyanophenyl;
   R' is a member selected from the group consisting of hydrogen, methyl and ethyl; and
   R" is a member selected from the group consisting of hydrogen and methyl.

2. A solution of claim 1 wherein said polar solvent is ethyl alcohol.

3. A solution of claim 1 wherein said solubilizing agent is selected from the group consisting of polyethylene glycol, dimethyl isosorbide, Polysorbate-20 and mixtures thereof.

4. A solution of claim 1 wherein said imidazole derivative is 1-[2,4-dichloro-β-(2,4-dichlorobenzyloxy)-phenethyl]-imidazole or 1-[2,4-dichloro-β-(2,4-dichlorobenzyloxy)phenethyl]-imidazole nitrate.

5. A solution of claim 4 wherein said solvent system consists essentially of from about 55 to 65% by weight of said system of a polar solvent comprising 55 to 75% by weight ethyl alcohol, 0 to 10% by weight benzyl alcohol, and 25 to 35% by weight water; from about 25 to 35% by weight of said system of polyethylene glycol having an average molecular weight of about 200; from about 0.2 to 5% by weight of said system of an amphoteric surfactant; and from about 0.5 to 5% by weight of said system of a cosmetic humectant.

6. A solution of claim 5 wherein said humectant is glycerine.

7. A solution of claim 5 wherein said surfactant is selected from the group consisting of Amphoteric-2, Amphoteric-17, Amphoteric-21, and alkali metal salts thereof.

* * * * *